United States Patent
Trewella et al.

[11] Patent Number: 6,090,989
[45] Date of Patent: Jul. 18, 2000

[54] ISOPARAFFINIC LUBE BASESTOCK COMPOSITIONS

[75] Inventors: Jeffrey C. Trewella, Kennett Square, Pa.; Thomas R. Forbus, Jr., Woodstown, N.J.; Zhaozhong Jiang, Thorofare, N.J.; Randall D. Partridge, Haddonfield, N.J.; Suzanne Elaine Schramm, Glen Mills, Pa.

[73] Assignee: Mobil Oil Corporation, Fairfax, Va.

[21] Appl. No.: 09/170,683

[22] Filed: Oct. 13, 1998

Related U.S. Application Data

[60] Provisional application No. 60/062,824, Oct. 20, 1997.

[51] Int. Cl.$^7$ .................................................. C10M 101/00
[52] U.S. Cl. ............................................. 585/13; 508/110
[58] Field of Search ............................... 508/110; 585/13

[56] References Cited

U.S. PATENT DOCUMENTS

| | | | |
|---|---|---|---|
| 4,500,417 | 2/1985 | Chen et al. | 208/111 |
| 4,704,491 | 11/1987 | Tsutsui et al. | 585/10 |
| 4,827,064 | 5/1989 | Wu | 585/10 |
| 4,906,350 | 3/1990 | Lucien et al. | 208/197 |
| 4,943,672 | 7/1990 | Hammer et al. | 585/737 |
| 5,059,299 | 10/1991 | Cody et al. | 208/27 |
| 5,107,054 | 4/1992 | Del Rossi et al. | 585/739 |
| 5,135,638 | 8/1992 | Miller | 208/27 |
| 5,246,566 | 9/1993 | Miller | 208/27 |
| 5,282,958 | 2/1994 | Santilli et al. | 208/111 |
| 5,306,860 | 4/1994 | Bigeard et al. | 585/737 |
| 5,362,378 | 11/1994 | Borghard et al. | 208/138 |
| 5,366,658 | 11/1994 | Hoppe et al. | 585/13 |
| 5,833,839 | 11/1998 | Wittenbrink et al. | 208/112 |
| 5,906,727 | 5/1999 | Wittenbrink et al. | 585/13 |
| 6,008,164 | 12/1999 | Aldrich et al. | 508/110 |

FOREIGN PATENT DOCUMENTS

| | | |
|---|---|---|
| 0 776 959 A2 | 6/1997 | European Pat. Off. |
| WO 97/21788 | 6/1997 | WIPO |

*Primary Examiner*—Ellen M. McAvoy

[57] ABSTRACT

A liquid hydrocarbon composition, containing paraffinic hydrocarbon components in which the extent of branching, as measured by the percentage of methyl hydrogens (BI), and the proximity of branching, as measured by the percentage of recurring methylene carbons which are four or more carbons removed from an end group or branch ($CH_2>4$), are such that:

(a) $BI - 0.5(CH_2>4) > 15$; and
(b) $BI + 0.85(CH_2>4) < 45$ as measured over said liquid hydrocarbon composition as a whole.

21 Claims, 3 Drawing Sheets

ISOPARAFFINIC LUBE BASESTOCK COMPOSITIONS

RELATED APPLICATIONS

This application claims priority under 35 U.S.C. §119 to U.S. provisional application No. 60/062,824 filed Oct. 20, 1997.

FIELD OF THE INVENTION

High performance, lubricating oil basestocks have been developed which posses unique compositional characteristics and which demonstrate superior low temperature performance properties.

BACKGROUND OF THE INVENTION

Premium, high performance, lubricant basestocks generally exhibit useful viscosities over a wide range of temperatures, have improved viscosity index, and demonstrate lubricity, thermal and oxidative stability, and pour point equal to or better than conventional mineral oils. Such advantageous rheological and performance properties enhance their performance in lubricant formulations relative to mineral oil-based formulations, including a wider operating temperature window. However, premium lubricant base stocks are more expensive to produce than conventional mineral oil lubricants.

Many researchers have investigated ways of converting relatively low value hydrocarbon feedstocks, such as natural gas, into higher value products, such as fuels and lubricants. Additionally, much investigation has been conducted into catalytically upgrading waxy hydrocarbon feedstocks, which have significant concentrations of straight chain paraffin components, into more useful products by hydroisomerization and dewaxing, processes which isomerize and crack the straight chain paraffin wax components of the feedstock, respectively.

Processes for the production of hydrocarbon fuels and lubricants from synthesis gas, a mixture of hydrogen and carbon monoxide, have been known for some time, and of them, the Fischer-Tropsch (FT) process is probably the best known. An account of the development of the process and its more notable characteristics is given in Kirk-Othmer, Encyclopedia of Chemical Technology, Third Edition, John Wiley & Sons, New York, 1980, Vol. 11, pp. 473–478.

In the FT process, synthesis gas, generally formed by partial oxidation of methane, is passed over a catalyst at elevated temperature and pressure to produce a number of carbon monoxide reduction products including hydrocarbons, alcohols, fatty acids and other oxygenated compounds. In favorable circumstances, oxygenated materials can comprise less than 1 percent of a total desired liquid product. The hydrocarbon product is highly paraffinic in nature and typically includes hydrocarbon gas, light olefins, gasoline, light and heavy fuel oils and waxy gas oils. Because the higher boiling fractions in the product are generally too waxy for general use either as liquid fuels or lubricants, further processing or upgrading is normally necessary before they can be used, either as such or by being added to the general pool of products. Advantageously, the FT products contain little, if any, of typical petroleum contaminants, such as aromatic compounds, cycloparaffinic compounds (naphthenes), sulfur compounds and nitrogen compounds, due to the relatively pure nature of the feedstocks: hydrogen and carbon monoxide, and ultimately, methane or natural gas.

U.S. Pat. No. 4,500,417 discloses conversion of the high boiling fraction of FT products by contact with a high-silica, large pore zeolite and a hydrogenation component to produce a distillate fraction and a lube fraction characterized by a high VI (viscosity index) and low pour point. Catalysts include zeolite Y, zeolite Beta, mordenite, ZSM-3, ZSM-4, ZSM-18 and ZSM-20.

U.S. Pat. No. 4,906,350 discloses a process for the preparation of a lubricating base oil with a high VI and a low pour point by catalytic dewaxing at least part of the hydrocrackate of a wax-containing mineral oil fraction over a zeolitic catalyst selected from among ZSM-5, ZSM-11, ZSM-23, ZSM-35, ZSM-12, ZSM-38, ZSM-48, offretite, ferrierite, zeolite beta, zeolite theta, zeolite alpha and mixtures thereof.

U.S. Pat. No. 4,943,672 discloses a process for hydroisomerizing FT wax to produce lubricating oil having a high VI and a low pour point by first hydrotreating the wax under relatively severe conditions and thereafter hydroisomerizing the hydrotreated wax in the presence of hydrogen on a particular fluorided Group VIII metal-on-alumina catalyst.

U.S. Pat. No. 5,059,299 discloses a method for isomerizing slack wax obtained from mineral oils and wax to form high VI, very low pour point lube oil basestocks by isomerizing over a Group VI–VIII on halogenated refractory metal oxide support catalyst, followed by solvent dewaxing.

U.S. Pat. Nos. 5,135,638 and 5,246,566 disclose wax isomerization processes for producing lube oil having excellent viscosity, VI and low pour point by isomerizing a waxy petroleum feed over a molecular seive having certain pore measurements and at least one Group VIII metal. Catalysts include SAPO-11, SAPO-31, SAPO-41, ZSM-22, ZSM-23 and ZSM-35.

U.S. Pat. No. 5,282,958 discloses a process for dewaxing a hydrocarbon feed including straight chain and slightly branched paraffins having 10 or more carbon atoms to produce a dewaxed lube oil using catalysts of a specified pore geometry and containing at least one Group VIII metal. The feedstock is contacted with the catalyst in the presence of hydrogen; exemplified catalysts include SSZ-32, ZSM-22 and ZSM-23.

U.S. Pat. No. 5,306,860 discloses a method of hydroisomerizing FT-derived paraffins over a series of catalysts, including a zeolite Y catalyst to form high VI, low pour point lube oils.

U.S. Pat. No. 5,362,378 discloses conversion of FT heavy end products with a platinum/boron-zeolite Beta catalyst having a low alpha activity to produce an extra high VI lube, which may then be dewaxed by conventional solvent dewaxing or by increasing the severity of the hydroisomerization step. European Pat. No. 0 776 959 A2 discloses a process for preparing lubricating base oils having a VI of at least 150 from a FT wax feed by first hydroisomerizing over a suitable catalyst in the presence of hydrogen and then either solvent or catalytically dewaxing the intermediate 390° C.+ fraction.

However, none of the references discussed above disclose or suggest preparation of liquid hydrocarbons of a specific and limited range of compositions having any particular combination of branching properties, which lead to highly desirable lubricating properties including an unexpected combination of high viscosity index and low pour point. In fact, none of the cited references even discloses or suggests measuring Branching Index (BI) or Branching Proximity, as discussed below.

U.S. Pat. No. 4,827,064 discloses high VI synthetic lubricant compositions of polyalphaolefins wherein a "branching ratio", $CH_3/CH_2$, is measured.

The disclosures of the U.S. patents described above are hereby incorporated by reference in their entireties.

SUMMARY OF THE INVENTIONI

A first object of the present invention is production of unique liquid hydrocarbon composition which may be useful as lubricant oil basestocks having useful low temperature viscometric properties.

Another object of the present invention is to provide an outlet for low value natural gas, by converting it to premium value lubricant basestocks by a combination of Fischer Tropsch synthesis, hydroisomerization and catalytic dewaxing steps.

One embodiment of the present invention is directed to a liquid hydrocarbon composition of paraffinic hydrocarbon components in which the extent of branching, as measured by the percentage of methyl hydrogens (BI), and the proximity of branching (or "Branching Proximity"), as measured by the percentage of recurring methylene carbons which are four or more carbons removed from an end group or branch ($CH_2>4$), are such that:

(a) $BI-0.5(CH_2>4)>15$; and (b) $BI+0.85(CH_2>4)<45$;

as measured over the liquid hydrocarbon composition as a whole.

Another embodiment of the present invention is directed to a lubricant oil basestock composition having paraffinic hydrocarbon components in which the extent of branching, as measured by the percentage of methyl hydrogens (BI), and the proximity of branching, as measured by the percentage of recurring methylene carbons which are four or more carbons removed from an end group or branch ($CH_2>4$), are such that:

(a) $BI-0.5(CH_2>4)>15$; and (b) $BI+0.85(CH_2>4)<45$;

as measured over the lubricant oil basestock composition as a whole.

In another embodiment, the present invention is directed to a lubricating oil composition of a liquid hydrocarbon composition having paraffinic hydrocarbon components in which the extent of branching, as measured by the percentage of methyl hydrogens (BI), and the proximity of branching, as measured by the percentage of recurring methylene carbons which are four or more carbons removed from an end group or branch ($CH_2>4$), are such that:

(a) $BI-0.5(CH_2>4)>15$; and (b) $BI+0.85(CH_2>4)<45$;

as measured over the liquid hydrocarbon composition as a whole, and optionally, effective amounts of lubricating oil additives such as, but not limited to, antioxidants, anti-wear additives, extreme pressure additives, friction modifiers, viscosity index improvers, pour point depressants, detergents, dispersants, corrosion inhibitors, metal deactivators, seal compatibility additives, demulsifiers, antifoam additives, and mixtures thereof.

DESCRIPTION OF THE DRAWINGS

The above and other objects, features and advantages of the present invention will be better understood from the following detailed descriptions, taken in conjunction with the accompanying drawings, all of which are given by illustration only, and are not limitative of the present invention.

DETAILED DESCRIPTION OF THE INVENTION

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

One embodiment of the present invention is directed to a liquid hydrocarbon composition of paraffinic hydrocarbon components in which the extent of branching, as measured by the percentage of methyl hydrogens (BI), and the proximity of branching, as measured by the percentage of recurring methylene carbons which are four or more carbons removed from an end group or branch ($CH_2>4$), are such that:

(a) $BI-0.5(CH_2>4)>15$; and (b) $BI+0.85(CH_2>4)<45$;

as measured over the liquid hydrocarbon composition as a whole.

The hydrocarbon fluids of the present invention preferably have BI greater than or equal to 25.4, and Branching Proximities ($CH_2>4$) less than or equal to 22.5, although any compostion meeting the limitations of formulae (a) and (b) is intended to be within the scope of the present invention.

Measurement of the branching characteristics of the liquid hydrocarbons according to the present invention was performed by nuclear magnetic resonance (NMR) analysis, and is described in more detail below.

The liquid hydrocarbon composition of the present invention may have very low concentration levels of typical contaminants found in lube oil basestocks refined from natural mineral oils, depending upon the nature of the feedstock used to produce the liquid hydrocarbons. Typically, the liquid hydrocarbon compositions of the present invention have less than 0.1 wt % aromatic hydrocarbons, less than 20 ppm by weight of nitrogen-containing compounds, less than 20 ppm by weight of sulfur-containing compounds and low levels of naphthenic hydrocarbons, i.e. cycloparaffins. It is expected that the levels of these contaminants may be much lower, or that they may be entirely absent from the inventive liquid hydrocarbons. Accordingly, the concentration levels of both sulfur and nitrogen compounds in the inventive hydrocarbon compositions, when derived from FT waxes, are preferably less than 10 ppm each, and more preferably less than 1 ppm each.

The low levels of sulfur- and nitrogen-containing compounds are primarily due to the nature of the feedstock. Use of Fischer-Tropsch waxes, formed from relatively pure synthesis gas mixtures which have little, if any, nitrogen- or sulfur-containing compounds in the gas phase results in hydrocarbon fluids having very low levels of typical contaminants. In contrast, naturally occuring mineral oils have substantial concentrations of organic sulfur and nitrogen compounds, which are difficult or impossible to remove by commercial physical separation techniques, such as distillation.

The reasons for the low levels of aromatics and naphthenics in the liquid hydrocarbons of the present invention are two-fold: First, Fischer-Tropsch derived feedstocks are inherently low in ring-containing molecules, as the conversion process produces primarily, and almost exclusively, linear carbon chains; second, careful selection of the hydrocarbon conversion catalysts and conditions used in the process of forming the present invention materials greatly reduces the formation of aromatics and naphthenes during hydroisomerization and catalytic dewaxing.

While it is preferable to produce the liquid hydrocarbons of the present invention from Fischer-Tropsch-derived materials in order to obtain the very low level of contaminants in the product fluids, other waxy hydrocarbon materials, such as conventional waxy lube raffinates, slack waxes, deoiled slack waxes, foots oils and lube distillate hydrocrackates may be used to form the hydrocarbon compositions of the present invention.

On average, the liquid hydrocarbon compositions of the present invention are paraffinic hydrocarbon components having fewer than 10 hexyl- or longer branches per 100 carbon atoms. Likewise, the liquid hydrocarbon compositions of the present invention are paraffinic hydrocarbon components having on average more than 16 methyl branches per 100 carbon atoms, The hydrodewaxing step used to produce the liquid hydrocarbons of the present invention results in significant levels of isomerization of the long chain paraffins in the waxy feedstocks, resulting in paraffinic hydrocarbon components with a plurality of branches, as described in formulae (a) and (b).

The hydrocarbon fluids of the present invention find use as lubricant oil basestocks, or as components of formulated lubricating oils, i.e. in combination with other lubricating oil basestocks, such as for example mineral oils, polyalphaolefins, esters, polyalkylenes, alkylated aromatics, hydrocrackates and solvent-refined basestocks.

In another embodiment, the present invention is directed to a lubricant oil basestock composition having paraffinic hydrocarbon components in which the extent of branching, as measured by the percentage of methyl hydrogens (BI), and the proximity of branching, as measured by the percentage of recurring methylene carbons which are four or more carbons removed from an end group or branch ($CH_2$>4), are such that:

(a) $BI-0.5(CH_2>4)>15$; and
(b) $BI+0.85(CH_2>4)<45$;

as measured over the lubricant oil basestock composition as a whole.

The lubricant oil basestocks of the present invention contain primarily isoparaffinic components with nominal boiling points of 370° C+ and are unusual in that they unexpectedly exhibit a unique combination of both high viscosity indices and extremely low pour points. These two characteristics are generally known in the art to be related in direct proportion, i.e. lowering the pour point of a hydrocarbon fluid results in decreasing the viscosity index, and therefore it is quite unusual to obtain both an extremely low pour point and a relatively high VI in the same fluid. For example, conventional mineral oil basestocks, such as Comparative Examples 3–5 herein, exhibit relatively low VI's when pushed into the low pour point ranges (Table 1).

However, the basestocks of the present invention are characterized by extremely low pour points (PP) of less than or equal to –18° C., preferably less than or equal to –30° C. and more preferably less than or equal to –40° C., with kinematic viscosities (KV) ranging from about 2.0 cSt to greater than about 13 cSt, preferably about 4 cSt to about 8 cSt, at 100° C. and high viscosity indices (VI) from about 130–165, preferably from about 140–165 and more preferably from about 150–165, as well as BI and $CH_2$>4 values as set forth in formulae (a) and (b), above.

In particular, preferred products of the present invention are lubricant oil basestocks having a combination of VI and pour point from about 130 VI/–66° C. to about 165 VI/–27° C. and more preferably from about 144 VI/–40° C. to about 165 VI/–27° C.

Hydrocarbon conversion catalysts useful in the conversion of the waxy feedstocks disclosed herein to form the hydrocarbon components of the present invention are zeolite catalysts, such as ZSM-5, ZSM-11, ZSM-23, ZSM-35, ZSM-12, ZSM-38, ZSM-48, offretite, ferrierite, zeolite beta, zeolite theta, zeolite alpha, as disclosed in U.S. Pat. No. 4,906,350. These catalysts are used in combination with Group VIII metals, in particular palladium or platinum. The Group VIII metals may be incorporated into the zeolite catalysts by conventional techniques, such as ion exchange.

The process of making the lubricant oil basestocks of the present invention may be characterized as a hydrodewaxing processes. The hydrodewaxing process may be conducted over a combination of catalysts, or over a single catalyst. Conversion temperatures may range from about 200° C. to about 500° C. at pressures ranging from about 500 to 20,000 kPa. This process is operated in the presence of hydrogen and hydrogen partial pressures will normally be from 600 to 6000 kPa. The ratio of hydrogen to the hydrocarbon feedstock (hydrogen circulation rate) will normally be from 10 to 3500 n.l.l.$^{-1}$ (56 to 19,660 SCF/bbl) and the space velocity of the feedstock will normally be from 0.1 to 20 LHSV, preferably 0.1 to 10 LHSV.

For example, conversion of the waxy feedstock may be conducted over a combination of Pt/zeolite Beta and Pt/ZSM-23 catalysts in the presence of hydrogen. Alternatively, the process of the producing the inventive lubricant oil basestocks may comprise hydroisomerization and dewaxing over a single catalyst, such as Pt/ZSM-35. In either case, the unique products of the present invention may be obtained.

In another embodiment, the present invention is directed to a lubricating oil composition of a liquid hydrocarbon composition having paraffinic hydrocarbon components in which the extent of branching, as measured by the percentage of methyl hydrogens (BI), and the proximity of branching, as measured by the percentage of recurring methylene carbons which are four or more carbons removed from an end group or branch ($CH_2$>4), are such that:

(a) $BI-0.5(CH_2>4)>15$; and
(b) $BI+0.85(CH_2>4)<45$;

as measured over the liquid hydrocarbon composition as a whole, and optionally, effective amounts of lubricating oil additives, such as for example antioxidants, anti-wear additives, extreme pressure additives, friction modifiers, viscosity index improvers, pour point depressants, detergents, dispersants, corrosion inhibitors, metal deactivators, seal compatibility additives, demulsifiers, anti-foam additives, and mixtures thereof.

A survey of conventional lubricant additives is provided in *Lubricants and Related Products,* by Dieter Klaman, in Chapter 9, pp. 177–217, Verlag Chemie GmbH (1984), which indicates some suitable antioxidants as phenolic or aromatic amines; as anti-rust additives benzotriazoles; metal deactivators such as ethylenediamines and imidazoles; VI improvers such as polyisobutenes and polymethacrylates; pour point depressants such as long-chain alkyl phenols and phthalic acid dialkylaryl esters. As dispersants, for example, poly-alkylene succinimides are disclosed; as detergents, compounds such as sulfonates, phenates, sulfurized phenates, phosphates and the like are disclosed. Also disclosed is the use of anti-wear agents and of extreme pressure additives, which may include organic sulfides, metal dithiocarbamates, chlorinated paraffins and organic phosphorous compounds, such as metal dithiophosphates; friction modifiers such as long-chain fatty acids, fatty alcohols and fatty esters; as antifoam additives, polydimethylsiloxanes and polyethylene glycol ethers and esters are known; as seal compatibility additives compounds such as aromatics, aldehydes, ketones and esters; as demulsifiers, dinonylnaphthalenesulfonates are known; and as corrosion inhibitors, tertiary amines, fatty acid amides, phosphoric acid derivatives and sulfonic acids are examples. The skilled artisan will be aware that many other such additive compounds are known in the art and might be useful with the base oils of the present invention.

The lubricating oil compositions of the present invention may contain other lubricating oil basestocks, such as mineral oils, polyalphaolefins, esters, polyalkylenes, alkylated aromatics, hydrocrackates and solvent-refined basestocks, in combination with the paraffinic hydrocarbon components described herein. The paraffinic hydrocarbon compositions of the present invention may be used as the majority base oil for a lubricating oil composition, with other more conventional lube oil basestocks added thereto, or may be used as an additive in combination with a major amount of another lube oil basestock. However, it is preferred that the liquid hydrocarbon compositions of the present invention be present at concentration levels of at least 5 wt % of the total lubricating basestock composition.

EXAMPLES

In the following examples, hydroisomerization and catalytic dewaxing reaction conditions were varied to obtain the desired products, with typical conditions ranging from, but not limited to, 200–370° C., 400–2000 psig, 0.50–2.0 hr$^{-1}$ LHSV, and 1900–5000 scf/B (standard cubic feet per barrel) H$_2$ at the reactor inlet.

Lube Basestock Physical Properties

Examples 1–4

A hydrogenated Fischer-Tropsch wax (Paraflint 80) was hydrodewaxed in the presence of hydrogen over a combination of Pt/zeolite Beta hydroisomerization catalyst and Pt/ZSM-23 selective dewaxing catalyst. Four different hydrocarbon fluids were obtained under increasingly severe processing conditions, having KV, VI and PP values as indicated in Table 1. Example 4 is an example of the present invention.

Examples 5 and 6

A hydrogenated and partially isomerized Middle Distillate Synthesis Waxy Raffinate (Shell MDS or "SMDS") was hydrodewaxed in the presence of hydrogen over the combination of catalysts used in Examples 1–4. Two different hydrocarbon fluids were obtained under increasingly severe processing conditions, having KV, VI and PP values as indicated in Table 1. Example 6 is an example of the present invention.

Examples 7–9

The Shell MDS feedstock of Examples 5 and 6 was hydrodewaxed over synthetic ferrierite in the presence of hydrogen, under varying severity conditions to produce three different hydrocarbon fluids, having KV, VI and PP values as indicated in Table 1. Examples 7–9 are all examples of the present invention.

Example 10

The waxy feedstock used in Examples 14 was hydrodewaxed over Pt/ZSM-48 in the presence of hydrogen to produce a hydrocarbon fluid having the KV, VI and PP ivalues indicated in Table 1. Example 10 is an example of the present invention.

Comparative Examples 1, 2, and 6

Commercially prepared polyalphaolefin basestocks of 3.87 cSt and 5.51 cSt KV at 100° C. are characterized by pour points of <-65° C. and VI's of 130 (Comparative Example 1) and 135 (Comparative Example 2), respectively. A commercial, higher viscosity grade of polyalphaolefin, 150 cSt KV at 100° C., is also included (Comparative Example 6).

Comparative Examples 3–5

Several commercially prepared basestocks derived from hydrocracked crude oil fractions were also evaluated. These included: A −1 8° C. pour point, 5.1 cSt KV@100° C., 147 VI Shell XHVI basestock derived from hydroisomerization of slackwax (Comparative Example 3); a 4.0 cSt KV@100° C., 114 VI Yukong 100 N basestock, characterized by a pour point of −15° C. (Comparative Example 4); and a 6.9 cSt KV@100° C., 102 VI Chevron RLOP 240 N basestock, also characterized by a pour point of −15° C. (Comparative Example 5).

Typical physical properties of various commercial lube basestocks are compared with those of the inventive ULPP (ultra-low pour point) FT isomerates in Table 1, below.

TABLE 1

BASESTOCK PROPERTIES

| Description | Kinematic Viscosity cSt@100° C. | Viscosity Index | Pour Point, ° C. |
|---|---|---|---|
| Paraflint C80 Wax (Feed) | 9.42 | — | 83 |
| Ex. 1 | 7.14 | 177 | 12 |
| Ex. 2 | 6.52 | 171 | −3 |
| Ex. 3 | 5.72 | 161 | −24 |
| Ex. 4* | 5.54 | 145 | −63 |
| SMDS Waxy Raffinate (Feed) | 5.07 | — | 39 |
| Ex. 5 | 5.23 | 142 | −24 |
| Ex. 6* | 5.11 | 130 | −66 |
| Ex. 7* | 5.33 | 149 | −18 |
| Ex. 8* | 5.23 | 136 | −59 |
| Ex. 9* | 5.46 | 144 | −40 |
| Ex. 10* | 7.9 | 157 | −42 |
| Comparative Examples | | | |
| C.E. 1 | 3.87 | 130 | <−65 |
| C.E. 2 | 5.51 | 135 | <−65 |
| C.E. 3 | 5.06 | 147 | −18 |
| C.E. 4 | 4.00 | 114 | −15 |
| C.E. 5 | 6.94 | 102 | −15 |
| C.E. 6 | 150 | 214 | −42 |

*Examples of the present invention

Figure 1:
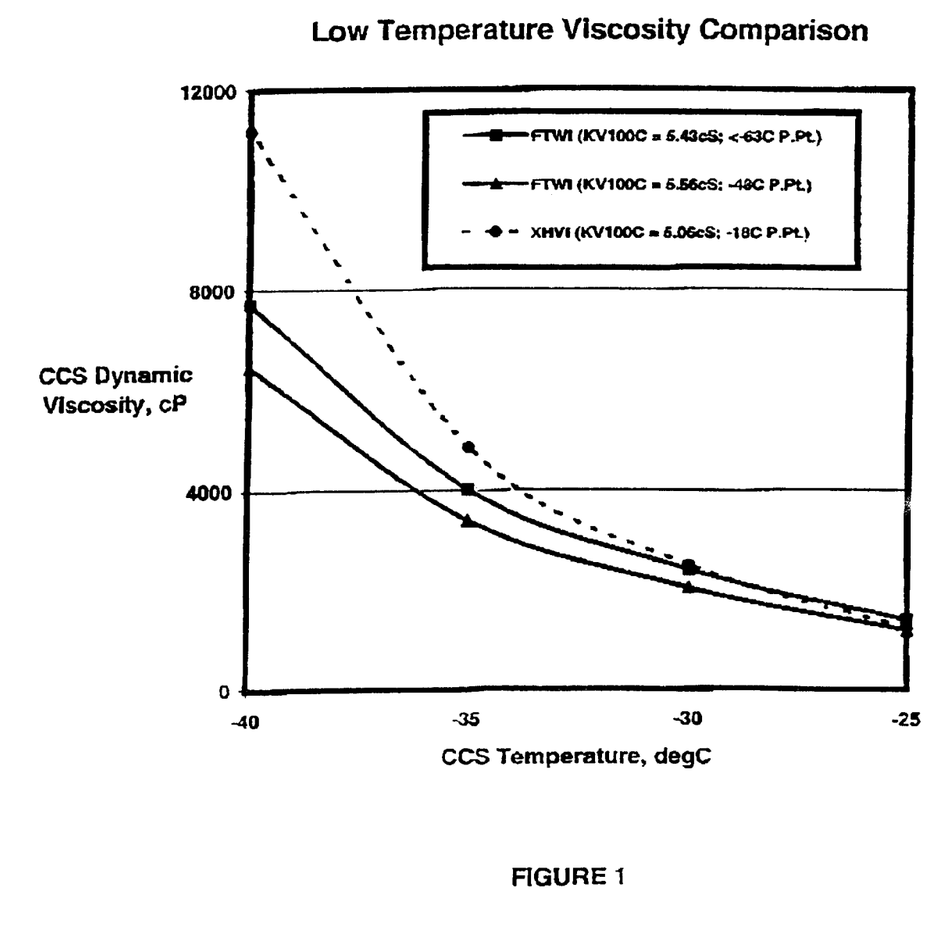
FIG. 1 is a graph comparing the low temperature viscometric properties of the liquid hydrocarbon compositions of the present invention with a typical hydroprocessed lubricant basestocks.

FIG. 1 is a graphic comparison of the Cold Crank Simulation (CCS) performances of a typical hydroprocessed hydrocarbon lube basestock (XHVI) and two basestocks according to the present invention. CCS testing was conducted according to ASTM method D5392, which is used to measure the apparent viscosity of motor oils. The CCS viscometer measures the dynamic viscosity of fluids at low temperature and low shear rate and stress, thus simulating the flow of oil in an engine crankcase at low temperature starting (cranking) conditions. The data of FIG. 1 demonstrates that the lubricant basestocks of the present invention have superior low temperature viscometric properties.

Measurement of Branching Characteristics
Branching Index (BI)

For each basestock indicated in Table 1, 359.88 MHz $^1$H solution NMR spectra were obtained on a Bruker 360 MHz AMX spectrometer using 10% solutions in CDCl$_3$. TMS was the internal chemical shift reference. CDCl$_3$ solvent gives a peak located at 7.28. All spectra were obtained under quantitative conditions using 90 degree pulse (10.9 µs), a pulse delay time of 30 s, which is at least five times the longest hydrogen spin-lattice relaxation time (T$_1$), and 120 scans to ensure good signal-to-noise ratios.

H atom types were defined according to the following regions:

9.2–6.2 ppm hydrogens on aromatic rings;
6.2–4.0 ppm hydrogens on olefinic carbon atoms;
4.0–2.1 ppm benzylic hydrogens at the α-position to aromatic rings;
2.1–1.4 ppm paraffinic CH methine hydrogens;
1.4–1.05 ppm paraffinic CH2 methylene hydrogens;
1.05–0.5 ppm paraffinic CH3 methyl hydrogens.

The branching index (BI) was calculated as the ratio in percent of non-benzylic methyl hydrogens in the range of 0.5 to 1.05 ppm, to the total non-benzylic aliphatic hydrogens in the range of 0.5 to 2.1 ppm. Results from these $^1$H NMR analyses are summarized in Table 2 below.

TABLE 2

% Different Types of H from $^1$H NMR

| Description | % CH$_3$ | % CH$_2$ | % CH | BI |
|---|---|---|---|---|
| Paraflint C80 Wax (Feed) | | | | |
| Ex. 1 | 19.4 | 78.5 | 2.1 | 19.4 |
| Ex. 2 | 22.3 | 76 | 1.7 | 22.3 |
| Ex. 3 | 25.6 | 71.8 | 2.6 | 25.6 |
| Ex. 4* | 27.6 | 68.1 | 4.3 | 27.6 |
| SMDS Waxy Raffinate (Feed) | 10.3 | 89.7 | 0 | 10.3 |
| Ex. 5 | 23.6 | 70.1 | 6.3 | 23.6 |
| Ex. 6* | 29.8 | 67.8 | 2.4 | 29.8 |
| Ex. 7* | 26.2 | 71.2 | 2.6 | 26.2 |
| Ex. 8* | 30 | 67 | 3 | 30 |
| Ex. 9* | 27.9 | 69.9 | 2.2 | 27.9 |
| Ex. 10* | 27 | 70.8 | 2.2 | 27 |
| Comparative Examples | | | | |
| C.E. 1 | 22.7 | 74.8 | 2.5 | 22.7 |
| C.E. 2 | 23.4 | 74.3 | 2.3 | 23.4 |
| C.E. 3 | 26.9 | 69.4 | 3.7 | 26.9 |
| C.E. 4 | 30.0 | 61.9 | 8.1 | 30.0 |
| C.E. 5 | 31.5 | 55.3 | 13.2 | 31.5 |
| C.E. 6 | 19.4 | 78.7 | 1.9 | 19.4 |

*Examples of the present invention

Branching Proximity (CH$_2$>4)

For each basestock indicated in Table 1, 90.5 MHz $^3$CMR single pulse and 135 Distortionless Enhancement by Polarization Transfer (DEPT) NMR spectra were obtained on a Bruker 360 MHz AMX spectrometer using 10% solutions in CDCl$_3$. TMS was the internal chemical shift reference. CDCl$_3$ solvent gives a triplet located at 77.23 ppm in the $^{13}$C spectrum. All single pulse spectra were obtained under quantitative conditions using 45 degree pulses (6.3 µs), a pulse delay time of 60 s, which is at least five times the longest carbon spin-lattice relaxation time (T$_1$), to ensure complete relaxation of the sample, 200 scans to ensure good signal-to-noise ratios, and WALTZ-16 proton decoupling.

The C atom types CH$_3$, CH$_2$, and CH were identified from the 135 DEPT $^{13}$C NMR experiment. A major CH$_2$ resonance in all $^{13}$C NMR spectra at ≈29.8 ppm is due to equivalent recurring methylene carbons which are four or more removed from an end group or branch (CH$_2$>4). The types of branches were determined based primarily on the $^{13}$C chemical shifts for the methyl carbon at the end of the branch or the methylene carbon one removed from the methyl on the branch. The proximity of branches, as indicated by CH$_2$>4, and the type of carbons are summarized in Table 3.

TABLE 3

% Different Types of C from $^{13}$C NMR

| Description | % CH$_3$ | % CH$_2$ | % CH | % CH$_2$>4 |
|---|---|---|---|---|
| Paraflint C80 Wax (Feed) | | | | |
| Ex. 1 | 13.6 | 81.3 | 5.1 | 38.2 |
| Ex. 2 | 15.7 | 78.6 | 5.7 | 28.8 |
| Ex. 3 | 17.3 | 76.3 | 6.3 | 22.5 |
| Ex. 4* | 18 | 75.5 | 6.5 | 14.7 |
| SMDS Waxy Raffinate (Feed) | 6.2 | 93.8 | 0 | 58.8 |
| Ex. 5 | 16.6 | 77.3 | 6 | 17.3 |
| Ex. 6* | 24.9 | 67.4 | 7.7 | 7.7 |
| Ex. 7* | 16.4 | 77.5 | 6.1 | 21.8 |
| Ex. 8* | 19.3 | 75.1 | 5.6 | 12.8 |
| Ex. 9* | 18.1 | 76.3 | 5.6 | 17.7 |
| Ex. 10* | 15.9 | 76.3 | 7.7 | 20.5 |
| Comparative Examples | | | | |
| C.E. 1 | 11.4 | 83.7 | 4.9 | 20.4 |
| C.E. 2 | 13.2 | 81 | 5.8 | 20.6 |
| C.E. 3 | 19 | 74.3 | 6.7 | 22.6 |
| C.E. 4 | 16.7 | 72.3 | 11 | 20.4 |
| C.E. 5 | 16.5 | 62 | 21.5 | 19.2 |
| C.E. 6 | 12.3 | 83.9 | 3.8 | 17.3 |

*Examples of the present invention

The branching characteristics and pour points of the isoparaffinic components of the exemplary basestocks, as disclosed in Tables 1–3, are compared in the following Table 4.

TABLE 4

Comparison of Isoparaffinic Lube Compositions

| Description | BI | % CH$_2$>4 | Pour Point, ° C. |
|---|---|---|---|
| Paraflint C80 Wax (Feed) | | | 83 |
| Ex. 1 | 19.4 | 38.2 | 12 |
| Ex. 2 | 22.3 | 28.8 | −3 |
| Ex. 3 | 25.6 | 22.5 | −24 |
| Ex. 4* | 27.6 | 14.7 | −63 |
| SMDS Waxy Raffinate (Feed) | 10.3 | 58.8 | 39 |
| Ex. 5 | 23.6 | 17.3 | −24 |
| Ex. 6* | 29.8 | 7.7 | −66 |
| Ex. 7* | 26.2 | 21.8 | −18 |
| Ex. 8* | 30 | 12.8 | −59 |
| Ex. 9* | 27.9 | 17.7 | −40 |
| Ex. 10* | 27 | 20.5 | −42 |
| Comparative Examples | | | |
| C.E. 1 | 22.7 | 20.4 | <−65 |
| C.E. 2 | 23.4 | 20.6 | <−65 |
| C.E. 3 | 26.9 | 22.6 | −18 |
| C.E. 4 | 30.0 | 20.4 | −15 |
| C.E. 5 | 31.5 | 19.2 | −15 |
| C.E. 6 | 19.4 | 17.3 | −42 |

*Examples of the present invention

The basestocks of the present invention can be differentiated from other hydrocarbon basestocks by the extent of branching as indicated by BI and the Branching Proximity as indicated by CH$_2$>4. These compositional fingerprints are graphed to aid in defining unique regions in this 2-dimensional composition space as illustrated in FIG. 2 (left quadrant).

Figure 2:
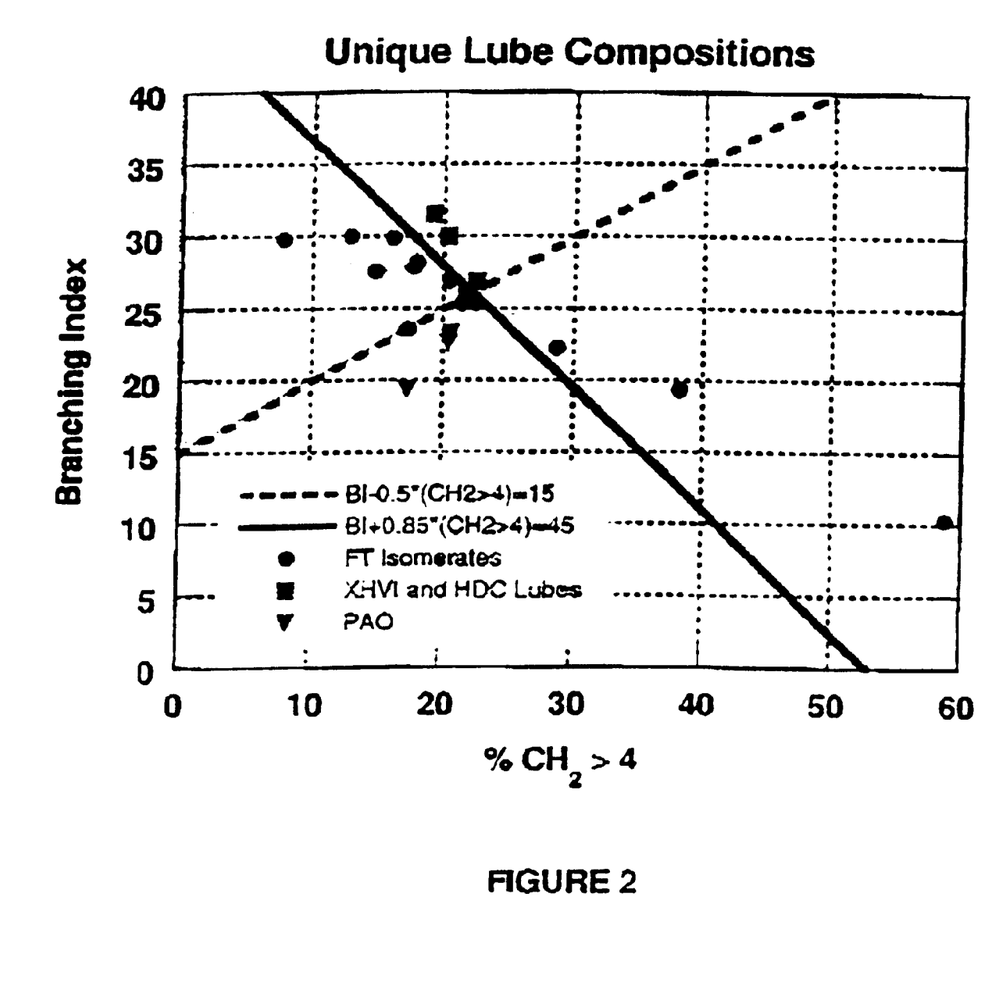
FIG. 2 is a graph mathematically illustrating the structural limitations of BI and $CH_2>4$, as set forth in formulae (a) and (b), which define the limits of the inventive compositions disclosed herein.
Figure 3:
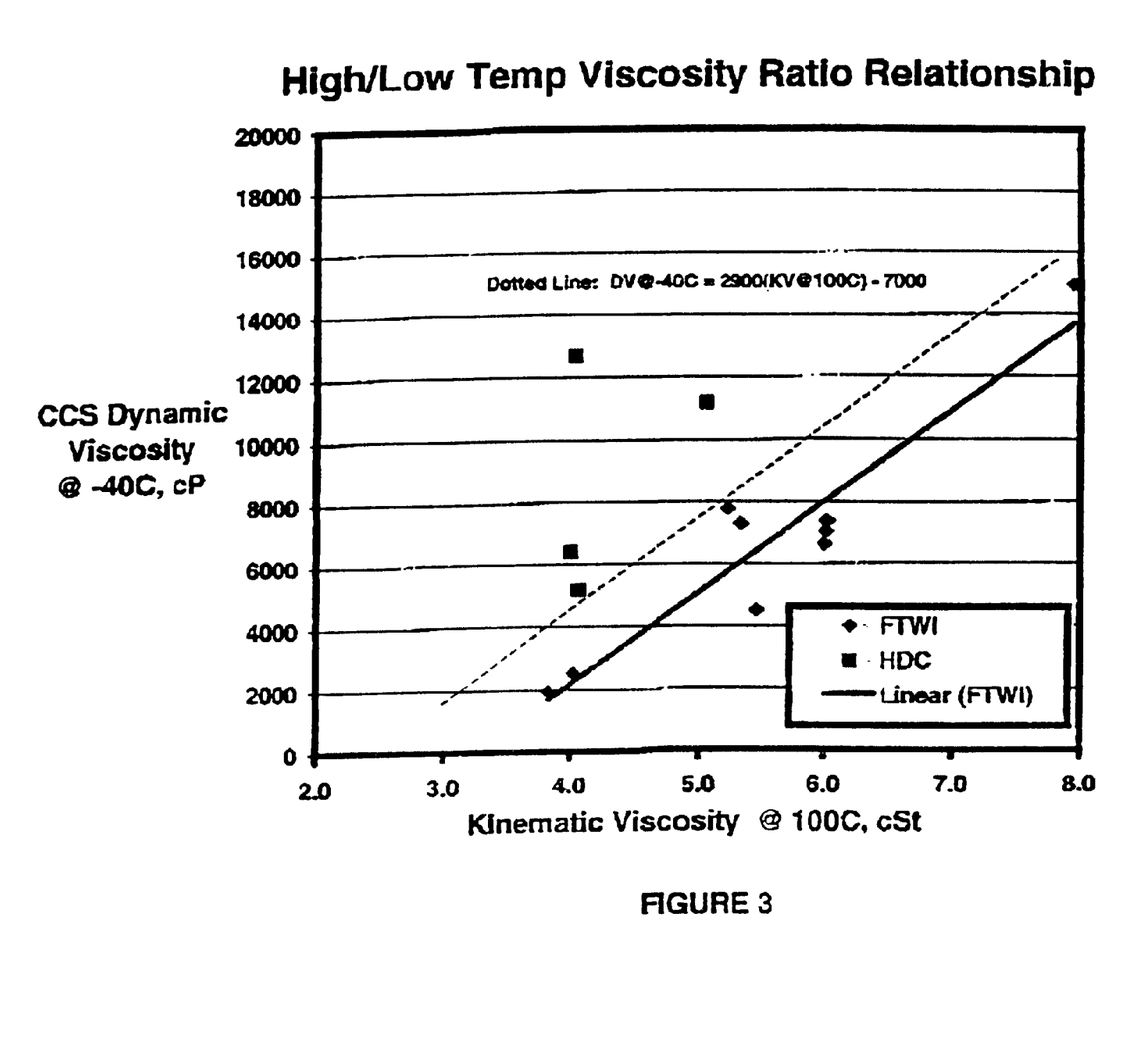
FIG. 3 is a graphic comparison of the dynamic viscosities (DV@–40° C.), measured by the CCS method ASTM D5392, and the kinematic viscosities (KV@100° C.) of various hydrocarbon fluids, including those of the present invention.

From FIG. 2 it is clear that the branching characteristics of the isoparaffinic basestock compositions of the present invention are within a unique region. Specifically, the composition can be described as comprising mixtures of paraffinic hydrocarbon components in which the extent of branching, as measured by the percentage of methyl hydrogens (BI), and the proximity of branching, as measured by the percentage of recurring methylene carbons which are four or more removed from an end group or branch (CH$_2$>4), are such that:

(a) BI−0.5(CH$_2$>4)>15; and (b) BI+0.85(CH$_2$>4)<45;

FIG. 3 is a graphic comparison of the dynamic viscosities (DV@−40° C.), measured by the CCS method, and the kinematic viscosities (KV@100° C.) of various hydrocarbon fluids, including those of the present invention. The fluids of the present invention are indicated as "FTWI" (Fischer Tropsch Wax Isomerate), while those conventional hydrocracked stocks are indicated as "HDC". In particular, the HDC data points represent Comparative Examples 3–5 of the present specification.

It is clear from the data set forth in FIG. 3 that the FTWI fluids of the present invention have significantly improved low-temperature viscosity characteristics compared to that of conventional HDC fluids of the prior art. Note that all of the liquid hydrocarbon fluids of the present invention fall below the dotted line on the graph and can therefore be described by the following equation:

(c) DV$_{@-40° C.}$<2900(KV$_{@100° C.}$)−7000.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A liquid hydrocarbon composition, comprising paraffinic hydrocarbon components in which the extent of branching, as measured by the percentage of methyl hydrogens (BI), and the proximity of branching, as measured by the percentage of recurring methylene carbons which are four or more carbons removed from an end group or branch (CH$_2$>4), are such that:

(a) BI−0.5(CH$_2$>4)>15; and (b) BI+0.85(CH$_2$>4)<45;

as measured over said liquid hydrocarbon composition as a whole.

2. The liquid hydrocarbon composition according to claim 1, which contains:

less than 0.1 wt % aromatic hydrocarbons;

less than 20 ppm (wt) nitrogen-containing compounds; and less than 20 ppm (wt) sulfur-containing compounds.

3. The liquid hydrocarbon composition according to claim 1, wherein the pour point of the composition is less than −18° C.

4. The liquid hydrocarbon composition according to claim 3, wherein the pour point of the composition is less than −30° C.

5. The liquid hydrocarbon composition according to claim 1, wherein said paraffinic hydrocarbon components have BI≧25.4 and (CH$_2$>4)≦22.5.

6. The liquid hydrocarbon composition according to claim 1, wherein said paraffinic hydrocarbon components have nominal boiling points of 370° C.+.

7. The liquid hydrocarbon composition according to claim 1, wherein said paraffinic hydrocarbon components comprise on average fewer than 10 hexyl- or longer branches per 100 carbon atoms.

8. The liquid hydrocarbon composition according to claim 1, wherein said paraffinic hydrocarbon components comprise on average more than 16 methyl branches per 100 carbon atoms.

9. The liquid hydrocarbon composition according to claim 1, wherein the combination of dynamic viscosity, as measured by CCS at −40° C., and kinetic viscosity as measured at 100° C. of said liquid hydrocarbon fluid are represented by the formula:

(c) DV$_{@-40° C.}$<2900(KV$_{@100° C.}$)−7000.

10. A lubricant basestock composition, comprising paraffinic hydrocarbon components in which the extent of branching, as measured by the percentage of methyl hydrogens (BI), and the proximity of branching, as measured by the percentage of recurring methylene carbons which are four or more carbons removed from an end group or branch (CH$_2$>4), are such that:

(a) BI−0.5(CH$_2$>4)>15; and (b) BI+0.85(CH$_2$>4)<45;

as measured over said lubricant basestock composition as a whole.

11. The lubricant basestock composition according to claim 10, which contains:

less than 0.1 wt % aromatic hydrocarbons;

less than 20 ppm (wt) nitrogen-containing compounds; and less than 20 ppm (wt) sulfur-containing compounds.

12. The lubricant basestock composition according to claim 10, wherein the pour point of the composition is less than −18° C.

13. The lubricant basestock composition according to claim 12, wherein the pour point of the composition is less than −30° C.

14. The lubricant basestock composition according to claim 10, wherein said paraffinic hydrocarbon components have BI≧25.4 and (CH$_2$>4)≦22.5.

15. The lubricant basestock composition according to claim 10, wherein said paraffinic hydrocarbon components have nominal boiling points of 370° C.+.

16. The lubricant basestock composition according to claim 10, wherein said P9 paraffinic hydrocarbon components comprise on average fewer than 10 hexyl- or longer branches per 100 carbon atoms.

17. The lubricant basestock composition according to claim 10, wherein said paraffinic hydrocarbon components comprise on average more than 16 methyl branches per 100 carbon atoms.

18. The lubricant basestock composition according to claim 10, wherein the combination of dynamic viscosity, as measured by CCS at −40° C., and kinetic viscosity as measured at 100° C. of said liquid hydrocarbon fluid are represented by the formula:

(c) DV$_{@-40° C.}$<2900(KV$_{@100° C.}$)−7000.

19. A lubricating oil composition, comprising a liquid hydrocarbon composition having a mixture of paraffinic hydrocarbon components in which the extent of branching, as measured by the percentage of methyl hydrogens (BI), and the proximity of branching, as measured by the percentage of recurring methylene carbons which are four or more carbons removed from an end group or branch ($CH_2>4$), are such that:

(a) $BI-0.5(CH_2>4)>15$; and
(b) $BI+0.85(CH_2>4)<45$;

as measured over said liquid hydrocarbon composition as a whole; and optionally, effective amounts of lubricating oil additives selected from the group consisting of antioxidants, anti-wear additives, extreme pressure additives, friction modifiers, viscosity index improvers, pour point depressants, detergents, dispersants, corrosion inhibitors, metal deactivators, seal compatibility additives, demulsifiers, anti-foam additives, and mixtures thereof.

20. The lubricating oil composition of claim 19, further comprising a lubricating oil basestock selected from the group consisting of mineral oils, polyalphaolefins, esters, polyalkylenes, alkylated aromatics, hydrocrackates and solvent-refined basestocks.

21. The lubricating oil composition of claim 20, wherein said liquid hydrocarbon composition is present at a concentration level of at least 5 wt % of the total lubricating basestock composition.

* * * * *